US006306838B1

(12) United States Patent
Singh et al.

(10) Patent No.: US 6,306,838 B1
(45) Date of Patent: Oct. 23, 2001

(54) **TARGETED VESICULAR CONSTRUCTS FOR CYTO PROTECTION AND TREATMENT OF *H. PYLORI***

(75) Inventors: Amarjit Singh; Rajesh Jain, both of New Delhi (IN)

(73) Assignee: Panacea Biotec Limited, New Delhi (IN)

( * ) Notice: Subject to any disclaimer, the term of this patent is extended or adjusted under 35 U.S.C. 154(b) by 0 days.

(21) Appl. No.: 09/490,127

(22) Filed: Jan. 24, 2000

(30) Foreign Application Priority Data

Jan. 25, 1999 (IN) .............................. 141/DEL/99

(51) Int. Cl.⁷ ...................... A61K 31/685; A61K 31/65; A61K 31/56
(52) U.S. Cl. .............................. 514/78; 514/152; 514/182
(58) Field of Search ................................ 514/78, 182, 152

(56) References Cited

U.S. PATENT DOCUMENTS 5,286,492 * 2/1994 Dettmar et al. ...................... 424/458

FOREIGN PATENT DOCUMENTS

| 676199 | 10/1995 | (EP) . |
| WO 95/28929 | 11/1995 | (WO) . |
| WO 95/28943 | 11/1995 | (WO) . |
| WO 95/31199 | 11/1995 | (WO) . |
| WO 96/24341 | 8/1996 | (WO) . |

OTHER PUBLICATIONS

Forman et al., *H Pylori* and Gastric Cancer, *The Lancet*, vol. 343, pp. 243–244, Jan. 22, 1994.

S. Carpenter–Green et al., Intercorporation of Acylated Wheat Germ Into Liposomes, *Analytical Biochemistry*, vol. 135, pp. 151–155, 1983.

A.A. Bogdanov, Jr., Lectin–Bearing Liposomes: Differential Binding to Normal and To Transformed Mouse Fibroblasts, *Experimental Cell Research*, vol. 181 (1989) 362–374.

J. R. Warren, Unidentified Curved Bacilli on Gastric Epithelium in Active Chronic Gastritis, *The Lancet*, pp. 1273–1275, Jun. 4, 1983.

B. J. Marshall et al., Unidentified Curved Bacilli in the Stomach of Patients With Gastritis and Peptic Ulceration, *The Lancet*, Jun. 16, 1984, pp. 1311–1315.

G. E. Buck et al., Relation of Campylobacter Pyloridis to Gastritis and Peptic Ulcer, *The Journal of Infectious Diseases*, vol. 153, No. 4, Apr. 1986, pp. 664–669.

F. J. Hutchinson et al., Lectin–Mediated Targeting of Liposomes to a Model Surface, *FEBS Letters*, vol. 234, No. 2, pp. 493–496, Jul. 1988.

D. Y. Graham, Campylobacter Pylori and Peptic Ulcer Disease, *Gastroenterology*, vol. 96, No. 2, 1989, pp. 615–625.

J. P. Liautard et al, Controlled Binding of Liposomes to Cultured Cells by Means of Lectins, *Cell Biology International Reports*, vol. 9, No. 12, Dec. 1985, pp. 1123–1137.

M. Kaszuba et al, The Preparation and Characterisation of Proteoliposomes for Targeting to Oral Bacteria, *Biochemical Society Transactions*, 1991.

C. S. Goodwin et al., Transfer of Campylobacter Pylori and Campylobacter Mustelae to Helicobacter Gen. Nov. As Helicobacter Pylori Comb. Nov. And Helicobacter Mustelae Comb. Nov., Respectively, *International Journal of Systematic Bacteriology*, Oct. 1989, p. 397–405, vol. 39, No. 4.

* cited by examiner

*Primary Examiner*—Kevin E. Weddington
(74) *Attorney, Agent, or Firm*—Oblon, Spivak, McClelland, Maier & Neustadt, P.C.

(57) ABSTRACT

A Novel Composition for targeted vesicular for treatment of H-Pylori infections and for protection of the cell is disclosed. The Composition Comprises Lectins, Phospholipids sterols an one or more drugs. The Composition is useful since not only it treats H-Pylori infections and other diseases associated therewith but also helps in protection of the cell walls.

12 Claims, 2 Drawing Sheets

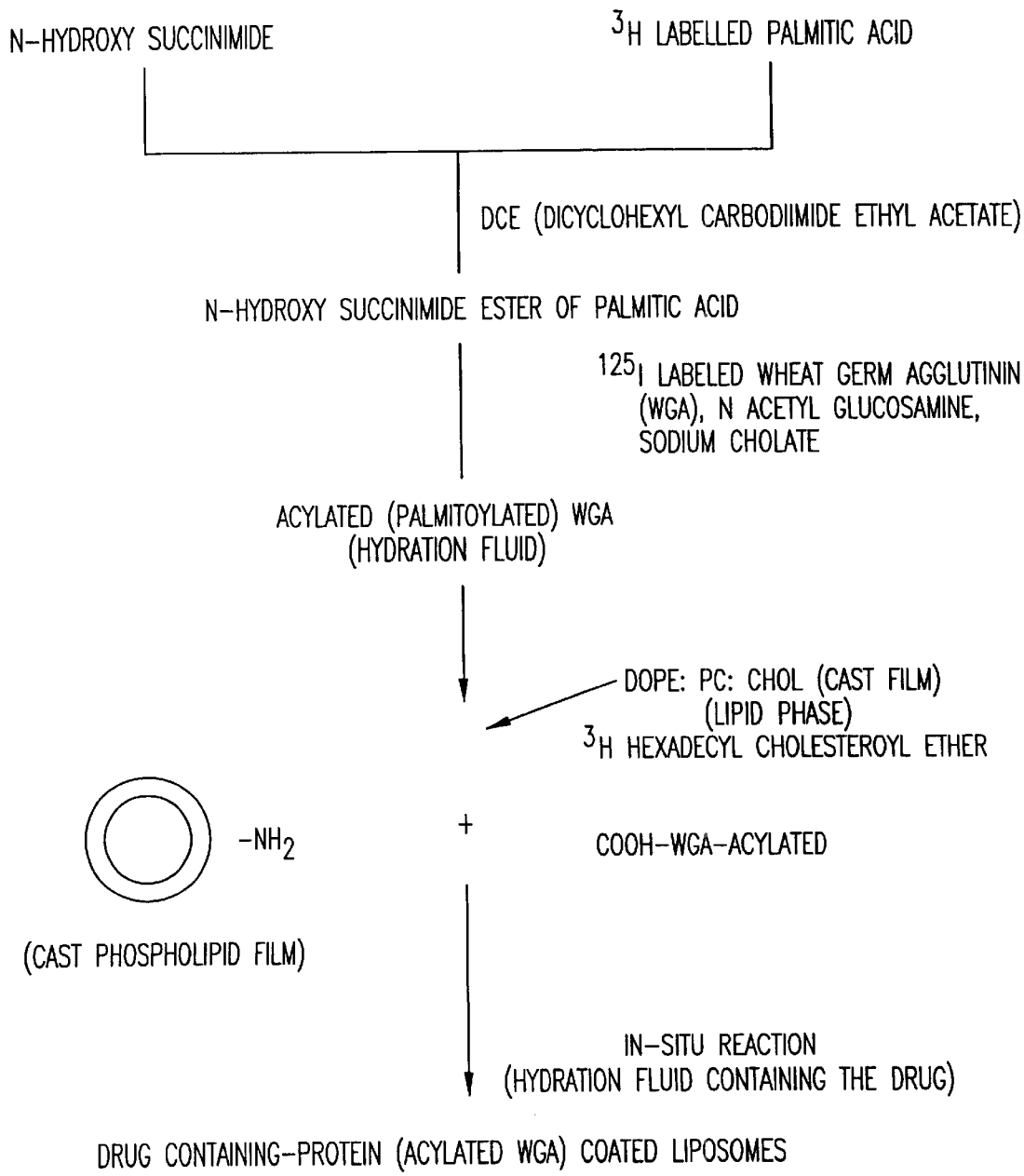
FIG.1: SCHEMATIC DIAGRAM REVEALING THE PROCESSING STEPS INVOLVED IN THE SYNTHESIS OF ACYLATED PROTEIN AND ITS CONJUGATION TO THE LIPOSOMAL SYSTEM

FIG. 2a

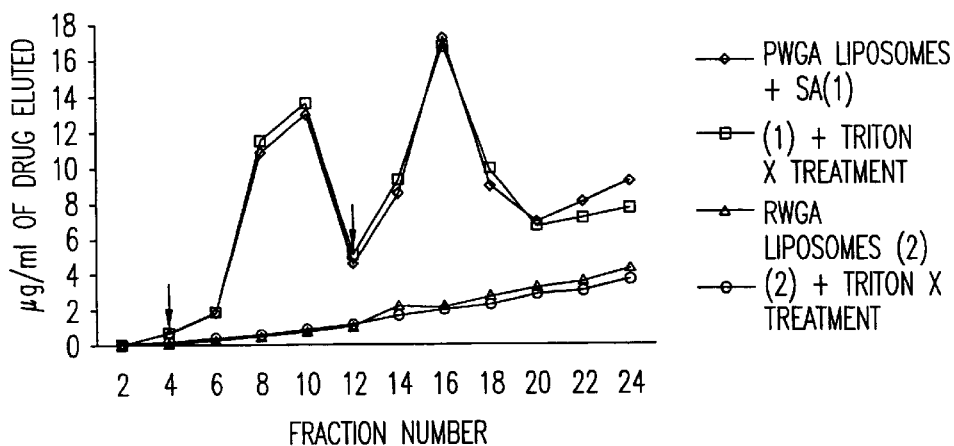

SIALIC ACID INDUCED INTERACTION OF THE SYSTEM IN A MINI-COLUMN USING EXOGENOUSLY SUPPLIED NeuNA (SIALIC ACID).
FIG.2a IS SHOWING THE STUDIES WITH PWGA COATED LIPOSOMES.

FIG. 2b

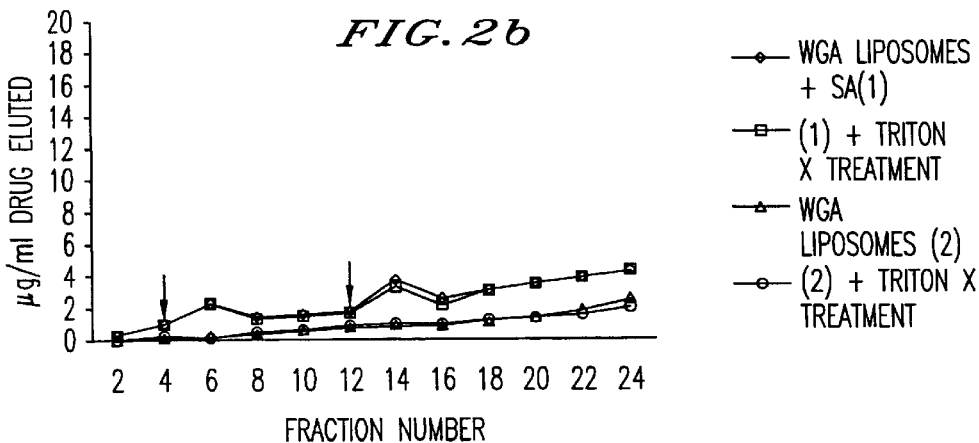

SIALIC ACID INDUCED INTERACTION OF THE SYSTEM IN A MINI-COLUMN USING EXOGENOUSLY SUPPLIED NeuNA (SIALIC ACID).
FIG.2b-THE STUDIES WITH WGA ADSORBED LIPOSOMES. INDICATES ADDITION OF SIALIC ACID IN THE LIPOSOMAL DISPERSION KEPT IN THE MINICOLUMN ASSEMBLY SIMULTANEOUSLY ANALYSING THE ELUENT FOR DRUG.

TARGETED VESICULAR CONSTRUCTS FOR CYTO PROTECTION AND TREATMENT OF H. PYLORI

INTRODUCTION

The present invention relates to a targeted vesicular composition for treatment of *H. pylori* infections and for cytoprotection.

BACKGROUND OF THE INVENTION

Excessive gastric acidity and mental stress were earlier thought to be major pathophysiological reasons for occurrence of peptic ulcers. Marshall and Warren (Warren., Lancet, 1: 1273–1275, 1983 and Marshall etal., Lancet, 2: 1311–1315, 1984) first reported an unidentified curved bacilli in the stomach of patients with gastric and peptic ulcers. These bacilli which were later identified as a gram negative spiral bacterium and named *Helicobactor pylori* (Goodwin et al., Int. J. Syst. Bacteriol. 39: 397–405, 1989), have been demonstrated to be associated with gastric and peptic ulcers (Buck et al., J. Infect. Dis. 153: 664–669, 1986 and Graham, Gastroenterology 96: 615–625, 1989).

The recognition that peptic ulcer is an infectious disease caused by the bacterium *H. pylori* has revolutionized the approach of diagnosis and therapy. *H. pylori* has been implicated in the etiology of chronic gastritis and peptic ulcer disease and also of gastric carcinoma and gastric mucosa associated lymphoid tissue lymphoma, if infection persists for a life time (Forman et al., Lancet, 343, 243–244, 1994). International agency for cancer research (IARC, USA), recently declared *H. pylori* to be a Group I carcinogen, a definite cause of human gastric cancers.

There are several patents that describe different methods to treat *H. pylori* infections. U.S. Pat. No. 5286492 describes the method of treatment of *H. pylori* with Triclosan. European patent no. 713392 describes the use of Clioquinol for treating *H. pylori* infections and related diseases. European patent no. 676199 describes the use of Trifloxacin or derivatives for the treatment of *H. pylori* infections. European patent no. 758245 describes the use of Spiramycin for treating gastrointestinal disorders caused by *H. pylori*. WIPO patent no. 9528929 describes the use of amino-N-oxide antimicrobials for use against *H. pylori* infections.

At present, the treatment of peptic ulcers with drugs like $H_2$-receptor antagonists, gastric acid, secretion inhibitors and mucosal protectants has been replaced partially or totally, by antibiotics/antimicrobials. Triple therapy regimen (Tetracycline, in combination with metronidazole and tripotassium dicitratobismuthate, TDB) has been found to be more effective than monotherapy, but patient compliance and drug resistance, further limits its applicability. Difficulties arise in the localization of the drug by conventional delivery systems, since they settle at the base of the stomach and are emptied along with gastric emptying. As a result, little amount of drug is delivered to the body or fundus of the stomach. Ecological niche of *H. pylori* due to the fact that it lies beneath the mucosal layers and develops rapid resistance to antibiotics (drug resistance towards the causative organism, originating either from the impermeability of the bacterial membrane envelope, or dye to production of β-lactamases), could be cited as reasons for the ineffectiveness of monotherapy and triple therapy (in some part) regimen. Systemic administration followed by local secretion in the gastric juice has been considered as an option for drug delivery to bacterium. Unfortunately, only strong bases diffuse into the stomach and the antibiotics used in *H. pylori* treatment being weak acids and bases, fail to enter the acid environment. There have been only a few drug delivery systems described, in prior art, to overcome problems of drugs used to treat *H. pylori* infections. WO/9624341 describes an approach to formulate drugs such as TDB in a chewing gum base for delivery to dental plaques and oral localized delivery. But this is a non-specific delivery and is not specifically targeted to *H. pylori* cells and suffers from the disadvantages of non-specificity. Moreover, many unpleasant tasting drugs may not be suitable for chewing gum dosage forms.

It is therefore appreciated that there is a need of novel delivery system which can combat with the biochemical and physico-chemical challenges encountered at infectious site (i.e., gastric mucosa) vis-a-vis presenting the system to the target cell lines with the help of specific ligands for the cell surface cytoporter system. Liposomes, the lipid bound microscopic vesicles have been used for targeting of the drugs to various target sites like fungal cells and cancerous cells. A great deal of research has been made on the ligand directed liposomal systems, mainly based on antibody mediated and carbohydrate mediated liposomal interactions. These have revealed some of the conceptual aspects of the enhanced in vitro and in-vivo stability and targeting potential as compared to native liposomes. Liposomes anchored with target-specific monoclonal antibody as a ligand are guided towards the cell surface antigens.

In our invention, we have adopted another novel strategy based on carbohydrate specific glycoconjugate ligands i.e. lectins. Lectins are proteins or glycoproteins that are capable of binding monosaccharidos, oligosaccharides and glycoproteins with an enzyme like specificity. The lectinized liposomes selectively approach their respective receptors expressed on to the surface of target cells. These receptors are cytoportals identified to be glyco-sphingolipids and glyco-proteins.

The carbohydrates recognition groups on the surface of target cells suggest the application of carbohydrate epitopes as ligands for intracytoplasmic targeted drug delivery. The concept of polyvalency or multivalency, i.e., binding to a target site through multiple interactions, viz. sugar affinity and specificity of membrane lectins for glyco-conjugates could be proposed as composite mechanisms. Among the glyco-conjugate linands, glycolipids, sphingoglycolipids, glycoproteins, lectins and polysaccharides are widely investigated pilot molecules to selective interact with biofilms and deliver the contents to cellular interiors. Lectinized liposomes have been used for targeting to HeLa cells (Liautard et al., Biol. Int. Rep., 2, 1123–1137, 1985), glycophorin—A biofilms (Hutchinson et al., FEBS Lett. 234, 493–496, 1988), mouse embryo and transformed fibroblast (Bogdanor et al., Exp. Cel. Res., 181: 362–375, 1989), chicken erythrocyte (Carpenter et al., Anal. Biochem., 135: 151–155, 1983), and Streptococcus infection (Kaszuba et al., Biochem. Soc. Trans., 19: 4165, 1991). Lectin appended liposomes interact selectively with the sugars expressed on cell surface as glycoconjugates. The specificity of the lectins for binding to a particular sugar has been appreciated as site directing component or character. The targeting could be negotiated via carbohydrate mediated interactions.

The multivalency characteristics of lectins impart to it, selectivity and affinity for bacterial cells. Appended ligands [lectins like Concanavallin A (Con A), Wheat germ agglutinin (WGA) and Rat cerebellum agglutinin (RCA)] owing to their sugar affinity and specificities, specifically adhere to the glycocalyx of the bacterial biofilm. The composition as described in this invention system, thus may selectively deliver the drug not only to the bacterial cell proximity but also via receptor mediated uptake in to cellular interiors.

The approach as described in this invention therefore, would be utilized to circumvent ulcerative and carcinogenesis associated with *H. pylori* infections in the upper GIT, simultaneously to steric protection and confer structural integrity to the disintegrated mucosal cell lines. The novel composition as described in the present invention is based on liposomes constituted using WGA acylated Phosphatidyl ethanolamine (PE) as film forming lipid component. PE itself fails forming bilayers (which usually adopts the hexagonal inverted micelle structure in preference to bilayer sheet) however, on derivatization with palmitoyl or acyl WGA/antibiodies it may form stable vesicular constructs entrapping water soluble susbstanits. On partitioning of acylated WGA-PE through ligand-receptor clustering, the system destabilizes and the contents are instantaneouly released. The lectin serves for ligands and recognizes its affinity receptor expressed on to the bacterial films. This as a result could place liposome on bacterial film releasing its antibacterial contents. In addition, the lipid components may serve as prostaglandin precursors or stimulus offering cytoprotection via inflamed site biochemistry manipulation.

SUMMARY OF THE INVENTION

The object of the proposed work was to engineer lipid vehicles using phosphatidylethanolamine and its derivatives as principle lipids. The derivative is subsequently utilized for keying of proteinaceous ligands to the surface. The acylated protein anchors impart bilayer stability to the liposomes. However, following subsequent receptor ligand interaction they dissociate leaving bilayers unstabilized. The consequence may beneficially be exploited for by-stander release of drug at the pre-selected site. Thus dual functionality of acylated proteins may lend the system a highly specific therapeutic potential. Furthermore, the protein ligands serve to confirm stability to the liposomes, especially, under bioenvironmental stresses of GI. The by-stander release under target derived stimulus specifies the system to be target sensitive, adding to its specificity and as a result improvises the monotherapy to the effective level. A further object was to provide prostaglandin precursor lipid constituents to heal and repair (cytoprotectlon and cytorepairing) the degenerated and disintegrated gastric mucosal cells of the infectious site.

In order to sum up the, objects, the engineered vesicular constructs encapsulating the antibiotic Amoxycillin in their aqueous domains were prepared using PE along with the different molar ratio of Phosphatidyl choline (PC): Cholesterol (Chol) and were stabilized using acylated protein based cap. The basic process is described in FIG. 1.

Lectin confers biochemical and physicochemical stability to the system. These vesicles resistant against gastric challenges, viz., pH and pepsin are capable of approaching target site (*H. pylori* induced ulcerated gastric mucosal site) through carbohydrate specific ligand associated with bacterial biofilm. Once these vesicles were presented to the bacterial cell surface, the structural integrity of the PE/PC based bilayers suffers reorientation releasing amoxycillin into the vicinity of the target cells or cellular interiors eradicating the causative organism. The lipid analog, PC may serve as prostaglandin precursor by providing essential fatty acids to the inflamed and degraded gastric mucosa and offer cytoprotection.

In accordance with the present invention there is disclosed a composition for curing *H. pylori* infections and for cytoprotection which comprises:

| | |
|---|---|
| Lectins | 1 to 20 mol % |
| Phospholipids | 20 to 80 mol % |
| Sterols | 0 to 50 mol % |
| One or more Drugs | 0.1 to 80 mol % |

DETAILED DESCRIPTION OF THE INVENTION

Liposomes are microscopic vesicles in which the aqueous milieu is enclosed in a single or multiple phospholipid bilayers (i) The liposomes can range from 30 nm to 50 $\mu$ in diameter. Depending upon the number of layers and size liposomes can be categorized into

| | |
|---|---|
| SUVs | Small Unilamellar liposomes |
| LUVs | Large Unilamellar liposomes |
| MLVs | Multilamellar liposomes |
| IUVs | Intermediate sized Unilamellar liposomes |
| MVVs | Multi vesicular vesicles |

The bilayers are generally composed of phospholipids along with sterols, added to impart rigidity and stability to the structures. Liposomes can be used to encapsulate both water-soluble as well as lipid soluble drugs.

Liposomes have great potential as drug delivery systems. They have been employed for the targeting of anticancer and antifungal agents with success.

*Helicobacter pylori* is the bactorium that has been implicated as the causative organism for chronic gastritis and peptic ulcer leading to gastric carcinoma and gastric mucosa associated lymphoid tissues lymphoma. The organism lies beneath the mucosal layer of the GIT and is also known to develop rapid resistance to antibiotics. For this reason, the commonly employed monotherapy or triple therapy regimens (Tetracycline, metronidazole and tripotassium dicitratobismuthate) proves ineffective.

We have utilized, here, the approach of targeting the surface of the target cells combined with the intracytoplasmic targeted drug delivery using liposomes, particularly the surface modifed, ligand coated liposomes have been employed.

These liposomes composed of phospholipids and cholesterol, containing amoxycillin in the aqueous compartment are stabilized using lectin. Lectin confers stability against gastric challenges, i.e., pH and pepsin. This allows the intact liposomes to reach the target cells, viz., the ulcerated mucosal site through the carbohydrate specific ligand associated with bacterial biofilm. On presentation to the bacterial cell surface, the membrane of the liposomes destabilizes and releases amoxycillin in the vicinity of the target cells or cellular interiors eradicating *H. pylori*. The constituents of the disrupted liposomal membrane i.e. phosphatidyl choline, in turn, serves as a cytoprotectant by providing essential fatty acids for the repair of the inflamed and degenerated gastric mucosa.

The preparation of liposomes was carried out as shown in the flow chart given in FIG. 1.

First of all, wheat germ agglutinin (WGA) was coupled with palmitic acid to yield Palmitoyl WGA (PWGA), by adapting the procedure by Green and Huang (Green, S. C.; Huang, L., Anal. Biochem. 136: 151–155, 1983). The resulting acylated WGA was added to the casted film prepared from phospholipids, i.e., dioleoyl phosphatidyl ethanolamine (DOPE) and/or dioleoyl phosphatidic acid (DOA) along with cholesterol (Chol) and sonicated to yield liposomes. The coating of the film with WGA was done either by covalent coating method using acylated WGA or charge induced coating using the underivatized WGA. Protein free liposomes were prepared for the purpose of comparison, using essentially the same procedure by lipid cast film method.

Separation of the unincorporated material was achieved by gel filtration column chromatography on a sephadex G-50-80 coarse column. The eluted fractions near the first peak in fractions 10–30 (corresponding to the void volume) were detected to contain the protein-coated liposomes and were collected. The unbound drug was eluted later in fractions 35–45. The developed liposomal system was subjected to linear sucrose gradient centrifugation study to separate the undervatized WGA from the liposomes.

Shape characteristics of the liposomes were studied by transmission electron microscopy (JEM 1200 EX 11, JEOL, Japan) using phosphotungstic acid as negative stain. Most of the liposomes were found to be multilamellar and spherical in shape. The particle size distribution was studied using dynamic laser light scattering technique (Autosizer IIC, Malvern Instruments, France). The average size of the liposomes was found to be 5.5 $\mu$.

The zeta potential of the liposomes was found using an elctrophoretic light scattering spectrophotometer (Zetasizer 4, Malvern Instruments, UK) and was found to range between 25 and 40 mV.

Encapsulation efficiency of the liposomes was determined by subjecting the pre-dialyzed suspension to centrifugation at 1,00,000 g for 60 minutes and washing the pellets with 0.01 M PBS (pH 7.4) thrice. The vesicles were lysed with triton X-100 and the drug content was measured spectrophotometrically. The encapsulation efficiency of liposomes was found to range between 31.8% and 40.5%. Liposomes stabilized with acylated proteins and with DOPE showed higher values as compared to those with adsorbed protein and plain liposomes.

Number of vesicles per $mm^3$ were counted using a haemocytometer with the help of photomicrographs (Leitz—Biomed, Germany) (Chatterjee, C.C., 1995, Human Physiology III ed., National Book Centre, Calcutta, India, 328). This parameter along with leaching of the drug was studied as an index for the stability of the liposomal suspension. In-vitro drug leaching from the liposomes was determined against phosphate saline buffer (pH 7.4) at 37° C. and 4° C., using equilibrium dialysis. The protein-coated system was found to be more stable both in terms of % vesicle count as well as tDI15 value (time for 15% drug leaching against dialysis in the medium) as compared to the uncapped formulation. Similar in-vitro studies were also conducted under pH, gastric pepsin, trypsin and α-chymotrypsin challenges. Even in SGF (simulated gastric fluid) the protein-coated systems were found to reveal better stability as compare to their plain version.

The ligand specificity of the liposomes towards sialic acid was determined by studying the elution profile of the liposomic dispersion in a mini-column with the milipore membrane at the base, before and after the addition of the sialic acid. The results of the sialic acid induced interaction of the developed system in vitro are shown in the FIG. 2.

The results of the study show that PWGA binds to the sialic acid, provided it is covalently bond to the liposomes. The destabilization of the bilayer membrane, once acylated WGA binds with free sialic acid is attributed to the pulse of drug released and ascribed to target responsive nature of liposomes.

In in-vitro studies, cell specificity of the liposomes was investigated using *Helicobacter pylori* cell lines. A marked enhancement in the binding of PWGA—liposomes as compared to plain liposomes or those prepared with WGA by adsorption method was observed. The results clearly reveal that binding specificity of liposomes to the target cells is distinctive and prominent in the case when acylated WGA was used for coating.

The cytorepairing and cytoprotective performance of the prepared liposomes was assessed in albino male rats of Wistar origin. The level of ulcer healing (%RUh) following the administration of liposomes against the NSAID induced castric lesions followed by colonization of gastric mucosa by orally delivered *H. felis* suspension culture was studied. The degree of ulceration and rate of ulcer healing was determined following the classification of Sakita (Sakita, T., Oguro, Y., Miwa, T., 1981, In: Handbook of Intestinal Endoscopy I ed., Tokyo: Chugi—Igakusha, 375–396) and Tamada (Tamada, F., 1992, In: Diagnostic and Therapeutic Gastrointestinal Endoscopy, KSH Hospital, 23–25). Histopathological examination of the gastric mucosa was done using phase contrast research microscope (Leitz—Biomed, Germany).

The results of the ulcer healing studies are given in Table 1.

The results reveal that among the various formulations tested, the system capped with acylated wheat germ agglutinin produced the best results. These capped liposomes achieved a nearly 95.8% recovery (ulcer healing) as compared to 33.3% recovery by amoxycillin at the same $MIC_{90}$ level. The photomicrographs confirmed the ulcer healing property of acylated WGA stabilized liposomes as they reveal the attachment of vesicles to the cell surface, followed by vesicular cytoprotection, which could be proposed to be mediated through ligand receptor interaction.

The expression "vesicular constructs" as used in this specification includes within its ambit "liposomes", "niosomes", "biosomes", "pharmacosomes" and its like.

In accordance with the present invention there is disclosed a composition for curing *H. pylori* infections and for cytoprotection which comprises:

| | |
|---|---|
| Lectins | 1 to 20 mol % |
| Phospholipids | 20 to 80 mol % |
| Sterols | 0 to 50 mol % |
| One or more Drugs | 0.1 to 80 mol % |

Lectins used in the present invention could be from plant, animal or any other source.

Lectins from plant source can be selected from Concanavalin A, Wheat Germ Agglutinin, Glycine A or can be obtained from *Tetragonolobus purpuria, Viscum album, Vigna radiata, Lens culinaris, Lathyrus odoratus.*

Lectins from animal source can be obtained from Human macrophages, Peritoneal lymphocytes, mouse peritoneal macrophages, B16 melanoma cell lines, Rat cerebellum, chicken thymus.

Phospholipids used in the present invention could be all phospholipids belonging to the category of Phosphatidyl choline, Phosphatidyl ethanolamine, Phosphatidyl serine, Phosphatidyl glycerol, Phosphatidyl acid and Phosphatidyl innositol, Sphingolipids.

Sterols used in the present invention could be Cholesterol, Ergosterol, Stigmasterol, Sitosterol.

Drugs used in the present invention could be all drugs used for *H. pylori* antimicrobial treatment such as antibiotics, $H_2$ receptor antagonists, protectants, astringents and antacids.

Antibiotics could be Amoxycillin, Clarithromycin, Tetracycline. Antiprotozoals could be Metronidazolo, Ornidazole. Protectants could be Bismuth and its salts. $H_2$ receptor Antagonists could be Omeprazole, Cimetidine and Ranitidine.

Formulation Details

EXAMPLE I

Dehydrated for Rehydration Type

| | |
|---|---|
| Palmitoylated Wheat Germ Agglutinin | 7 parts mol % |
| Dioleoyl Phosphatidyl Ethanolamine | 7 parts mol % |
| Phosphatidyl Choline | 48 parts mol % |
| Cholesterol | 14 parts mol % |
| Amoxycillin or its salt | 22 parts mol % |
| Excipients | 2 parts mol % |
| Total | 100 parts |

1. Palmitoylated Wheat Germ Agglutinin was coupled with Dioleoyl phosphatidyl ethanolamine by incubation at RT for 24 hours. Gel filtration chromatography using Sephadex column was conducted to purify the adduct in Phosphate Buffer. The solution was freeze-dried.
2. The freeze dried adduct was taken along with Phosphatidyl Choline and Cholesterol dissolved in diethyl ether and casted as lipid film.
3. The casted film was hydrated using Amoxycillin solution.
4. The mixture of step 3 was incubated for 2 hours and sonicated for 10 minutes in 2 cycles.
5. The step 4 was dialysed and/or centrifuged to remove free drug and lyophilized.
6. A constant $N_2$ umbrella was maintained throughout the whole process.

EXAMPLE II

Dehydrated for Reconstitution Type

| | |
|---|---|
| Dioleoyl Phosphatidyl Ethanolamine | 7 parts mol % |
| Phosphatidyl Choline | 48 parts mol % |
| Cholesterol | 14 parts mol % |
| Metronidazole | 22 parts mol % |
| Palmitoylated Wheat Germ Agglutinin | 7 parts mol % |
| Excipients | 2 parts mol % |
| Total | 100 parts |

1. Dioloyl phosphatidyl ethanolamine Phosphatidyl choline and Cholesterol was dissolved in diethyl ether. The solvent was evaporated to cast a thin film of lipids.
2. The casted film was hydrated using Metronidazole in a buffer.
3. The mixture of step 2 was incubated for 24 hours for hydration. The hydrated suspension was sonicated for 10 minutes.
4. Palmitoylated wheat germ agglutinin was added and the mixture was incubated for another 12 hours and then dialysed and lyophilized.
5. A constant $N_2$ umbrella was maintained throughout the whole process.

EXAMPLE III

| | |
|---|---|
| Dioleoyl Phosphatidyl Ethanolamine | 4 parts mol % |
| Dioleoyl Phosphatidic Acid | 4 parts mol % |
| Cholesterol | 23 parts mol % |
| Phosphatidyl Choline | 44 parts mol % |
| Palmitoylated Wheat Germ Agglutinin | 8 parts mol % |
| Ranitidine HCl | 16 parts mol % |
| Excipients | 1 parts mol % |
| Total | 100 parts |

1. Dioleoyl phosphatidyl ethanolamine, Dioleoyl phosphatidic acid, Cholesterol, Phosphatidyl choline were dissolved in diethyl ether. The solvent was evaporated to cast a thin film of lipids.
2. Palmitoylated Wheat Germ Agglutinin was added to the casted film and mixture was incubated for 12 hours.
3. The mixture of step 2 was hydrated using Ranitidine HCl solution in a buffer and incubated for 24 hours.
4. The hydrated suspension was sonicated for 10 minutes and then dialyzed and lyophilized.
5. A constant $N_2$ umbrella was maintained throughout the whole process.

EXAMPLE IV

| | |
|---|---|
| Dioleoyl Phosphatidyl Ethanolamine | 7 parts mol % |
| Dioleoyl Phosphatidic Acid | 7 parts mol % |
| Phosphatidyl Choline | 28 parts mol % |
| Cholesterol | 14 parts mol % |
| Palmitoylated Wheat Germ Agglutinin | 14 parts mol % |
| Amoxycillin or its salt | 28 parts mol % |
| Excipients | 2 parts mol % |
| Total | 100 parts |

1. Dioleoyl phosphatidyl ethanolamine, Dioleoyl phosphatidic acid, Cholesterol, Phosphatidyl choline were dissolved in diethyl ether. The solvent was evaporated to cast a thin film of lipids.
2. The cast film was hydrated using Amoxycillin solution in a buffer and incubated for 24 hours.
3. Palmitoylated wheat germ agglutinin was added to the mixture of step 2 and was incubated for 12 hours.
4. The hydrated suspension was sonicated for 10 minutes and then dialyzed and lyophilized.
5. A constant $N_2$ umbrella was maintained throughout the whole process.

EXAMPLE V

Ready to Use

| | |
|---|---|
| Distearoyl Phosphatidyl Choline (DSPC) | 20 parts mol % |
| Phosphatidyl Choline | 20 parts mol % |
| Cholesterol | 20 parts mol % |
| Phosphatidyl Ethanolamine | 10 parts mol % |
| Palmitoylated Wheat Germ Agglutinin | 10 parts mol % |
| Ranitidine HCl | 18 parts mol % |
| Excipients | 2 parts mol % |
| Total | 100 parts |

1. Distearoyl phosphatidyl choline, Cholesterol, Phosphatidyl choline, Phosphatidyl ethanolamine were dissolved in diethyl ether. The solvent was evaporated to cast a thin film of lipids.

2. The cast film was hydrated using Ranitidine HCl solution in a buffer and incubated for 24 hours.
3. Palmitoylated wheat germ agglutinin was added to the mixture of step 2 and was incubated for 12 hours.
4. The hydrated suspension was sonicated for 10 minutes and then dialyzed and lyophilized.
5. A constant $N_2$ umbrella was maintained throughout the whole process.

EXAMPLE VI

| | |
|---|---|
| Distearoyl Phosphatidyl Choline (DSPC) | 23 parts mol % |
| Phosphatidyl Choline | 23 parts mol % |
| Cholesterol | 12 parts mol % |
| Phosphatidic Acid | 5 parts mol % |
| Tetracycline HCl | 23 parts mol % |
| Palmitoylated Wheat Germ Agglutinin | 10 parts mol % |
| Excipients | 4 parts mol % |
| Total | 100 parts |

1. Distearoyl phosphatidyl choline, Cholesterol, Phosphatidyl choline, Phosphatidic acid were dissolved in diethyl ether. The solvent was evaporated to cast a thin film of lipids.
2. The cast film was hydrated using Tetracycline HCl solution in a buffer and incubated for 2 hours at 450° C.
3. Palmitoylated wheat germ agglutinin was added to the mixture of step 2 and was incubated for 12 hours.
4. The hydrated suspension was sonicated for 10 minutes and then dialyzed and lyophilized.
5. A constant $N_2$ umbrella was maintained throughout the whole process.

EXAMPLE VII

| | |
|---|---|
| Dimyristoyl Phosphatidyl Choline (DMPC) | 15 parts mol % |
| Distearoyl Phosphatidyl Choline (DSPC) | 15 parts mol % |
| Phosphatidic Acid | 8 parts mol % |
| Cholesterol | 15 parts mol % |
| Palmitoylated Wheat Germ Agglutinin | 15 parts mol % |
| Bismuth Phosphate | 30 parts mol % |
| Excipients | 2 parts mol % |
| Total | 100 parts |

1. Dimyristoyl phosphatidyl choline, Distearoyl phosphatidyl choline, Phosphatidic acid, Cholesterol were dissolved in diethyl ether. The solvent was evaporated to cast a thin film of lipids.
2. The cast film was hydrated using Bismuth Phosphate solution in a buffer and incubated for 2 hours at 45° C.
3. Palmitoylated wheat germ agglutinin was added to the mixture of step 2 and was incubated for 12 hours.
4. The hydrated suspension was sonicated for 10 minutes and then dialyzed and lyophilized.
5. A constant $N_2$ umbrella was maintained throughout the whole process.

EXAMPLE VIII

| | |
|---|---|
| Distearoyl Phosphatidyl Choline (DSPC): | 20 parts mol % |
| Phosphatidyl Choline | 20 parts mol % |
| Cholesterol | 10 parts mol % |
| Phosphatidic Acid | 10 parts mol % |
| Dioleoyl Phosphatidyl Ethanolamine | 10 parts mol % |

-continued

| | |
|---|---|
| Palmitoylated Wheat Germ Agglutinin | 10 parts mol % |
| Cimetidine HCl | 19 parts mol % |
| Excipients | 1 parts mol % |
| Total | 100 parts |

1. Distearoyl phosphatidyl choline, Phosphatidyl choline, Phosphatidic acid, Cholesterol were dissolved in diethyl ether. The solvent was evaporated to cast a thin film of lipids.
2. The cast film was hydrated using Cimetidine HCl solution in a buffer and incubated for 2 hours at 45° C.
3. Palmitoylated wheat germ agglutinin was added to the mixture of step 2 and was incubated for 12 hours.
4. The hydrated suspension was sonicated for 10 minutes and then dialyzed and lyophilized.
5. A constant $N_2$ umbrella was maintained throughout the whole process.

EXAMPLE IX

| | |
|---|---|
| Dioleoyl Phosphatidyl Ethanolamine | 4 parts mol % |
| Dioleoyl Phosphatidic Acid | 4 parts mol % |
| Cholesterol | 20 parts mol % |
| Phosphatidyl Choline | 41 parts mol % |
| Palmitoylated Wheat Germ Agglutinin | 8 parts mol % |
| Clarithromycin | 32 parts mol % |
| Excipients | 1 parts mol % |
| Total | 100 parts |

1. Dioleoyl phosphatidyl ethanolamine, Dioleoyl phosphatidic acid, Cholesterol, Phosphatidyl choline were dissolved in diethyl ether. The solvent was evaporated to cast a thin film of lipids.
2. Palmitoylated wheat germ agglutinin was added to the casted film and mixture was incubated for 12 hours.
3. The mixture of step 2 was hydrated using Clarithromycin solution in a buffer and incubated for 24 hours.
4. The hydrated suspension was sonicated for 10 minutes and then dialyzed and lyophilized.
5. A constant $N_2$ umbrella was maintained throughout the whole process.

EXAMPLE X

| | |
|---|---|
| Dioleoyl Phosphatidyl Ethanolamine | 10 parts mol % |
| Dioleoyl Phosphatidic Acid | 7 parts mol % |
| Phosphatidyl Choline | 40 parts mol % |
| Cholesterol | 26 parts mol % |
| Palmitoylated Wheat Germ Agglutinin | 14 parts mol % |
| Omeprazole Sodium | 1 parts mol % |
| Excipients | 2 parts mol % |
| Total | 100 parts |

1. Dioleoyl phosphatidyl ethanolamine, Dioleoyl phosphatidic acid, Cholesterol, Phosphatidyl choline were dissolved in diethyl ether. The solvent was evaporated to cast a thin film of lipids.
2. The cast film was hydrated using Omeprazole solution in a buffer and incubated for 24 hours.
3. Palmitoylated wheat germ agglutinin was added to the mixture of step 2 and was incubated for 12 hours.
4. The hydrated suspension was sonicated for 10 minutes and then dialyzed and lyophilized.

5. A constant $N_2$ umbrella was maintained throughout the whole process.

TABLE 1

% Rate of ulcer healing calculated for the developed systems using Sakita's classification

| Group(S) | No. of ulcers recovered (S2) | Total no. of ulcers (A1 + A2 + H1 + H2 + S1 + S2) | % Rats with ulcers | % Rate of ulcer healing |
|---|---|---|---|---|
| I | 0 | 24 | 100.0 ± 0.01 | 0.00 |
| II | 8 | 24 | 54.15 ± 0.1 | 33.3 ± 1.2 |
| III | 14 | 24 | 37.5 ± 0.6 | 54.16 ± 0.8 |
| IV | 16 | 24 | 16.7 ± 0.2 | 66.7 ± 0.1 |
| V | 19 | 24 | 4.16 ± 0.3 | 79.1 ± 0.7 |
| VI | 22 | 24 | 0.0 ± 0 | 91.6 ± 1.1 |
| VII | 23 | 24 | 0.0 ± 0 | 95.8 ± 0.7 |

I = control; III = Protein free (plain) liposomes PL; IV = Protein coated liposomes (charge induced absorption) WGAL; V,VI and VII = Protein coated liposomes (covalently linked with Acylated WGA with different lipid mole fractions PC: Chol. DOPE/DOPA) PWGAL. V (PC:Chol: DOPE; 2:1:1) VI (PC: Chol: DOPE + DOPA 6:3:1) VII (PC:Chol: DOPE + DOPA ; 2:1:1)

We claim:

1. A composition which comprises

| one or more lectins | 1 to 20 mol % |
|---|---|
| one or more phospholipids | 20 to 80 mol % |
| one or more sterols | 0 to 50 mol % |
| one of more drugs | 0.1 to 80 mol % |

2. A composition as claimed in claim 1 in the form of a vesicular construct which is selected from the group consisting of liposomes, pharmacosomes, niosomes and biosomes, or combinations thereof.

3. A composition as claimed in claim 1 wherein said one or more lectins are obtained from plant or animal sources, or combinations thereof.

4. A composition as claimed in claim 3 wherein said plant lectins are Concanavalin A, Wheat Germ Agglutinin or Glycine A or are obtained from *Tetragonolobus purpuria, Viscum album, Vigna radiata, Lens culinaris Lathyrus odoratus*, or combinations thereof.

5. A composition as claimed in claim 3 wherein said animal lectins are obtained from animal sources selected from the group consisting of human macrophages, peritoneal lymphocytes, mouse peritoneal macrophages, B16 melanoma cell lines, rat cerebellum and chicken thymus, or combinations thereof.

6. A composition as claimed in claim 1 wherein said one or more phospholipids are selected from the group consisting of Phosphatidyl Choline, Phosphatidyl Ethanolamine, Phosphatidyl Serine, Phosphatidyl Glycerol, Phosphatidyl Acid, Phosphatidyl Innositol and Sphingolipids, or combinations thereof.

7. A composition as claimed in claim 1 wherein said one or more sterols are selected from the group consisting of Cholesterol, Ergosterols, Stigmasterols and Sitosterols, or combinations thereof.

8. A composition as claimed in claim 1 wherein said one or more drugs are all drugs for disease conditions associated with *H.Pylori*.

9. A composition as claimed in claim 8 wherein the said one or more drugs are Antibiotics, Antiprotozoals, $H_2$ receptor Antagonists, Protectants, Astringents or Antacids, or combinations thereof.

10. A composition as claimed in claim 9 wherein the Antibiotics are Amoxycillin, Clarithromycin or Tetracycline, or combinations thereof, Antiprotozoals are Metronidazole or Ornidazole, or combinations thereof, Protectants are Bismuth and its salts, or combinations thereof, $H_2$ receptor Antagonists are Omeprazole, Cimetidine or Ranitidine, or combinations thereof.

11. A method for treatment of *Helicobactor pylori* infection, cytorepair or cytoprotection, or combinations thereof, which comprises administering the composition of claim 1 to a human or an animal.

12. A method for treatment of *Helicobactor pylori* infection, cytorepair or cytoprotection, or combinations thereof, which comprises administering the composition of claim 2 to a human or an animal.

* * * * *